United States Patent [19]

Nudelman et al.

[11] Patent Number: 4,855,417
[45] Date of Patent: Aug. 8, 1989

[54] ANOMERIC DEACETYLATION

[75] Inventors: Abraham Nudelman, Rehovot; Jaacov Herzig, Raanana; Ehud Keinan, Holon, all of Israel

[73] Assignee: Yeda Research and Development Company Ltd, Rehovot, Israel

[21] Appl. No.: 942,432

[22] Filed: Dec. 11, 1986

[30] Foreign Application Priority Data

Dec. 12, 1985 [IL] Israel ........................................ 73307

[51] Int. Cl.$^4$ ........................ C07H 15/04; C07H 1/00
[52] U.S. Cl. .................................... 536/121; 536/1.1; 536/4.1; 536/124
[58] Field of Search .................. 536/4.1, 121, 124, 1.1

[56] References Cited

PUBLICATIONS

Watanabe et al., Chemical Abstracts vol. 107, No. 134553u.

*Primary Examiner*—Johnnie R. Brown
*Assistant Examiner*—Elli Peselev
*Attorney, Agent, or Firm*—Browdy and Neimark

[57] ABSTRACT

There is provided a process for the selective anomeric deacetylation of sugar derivatives, which may be substituted by substituents such as acetoxy, chloracetoxy, alkoxy, azido, etc., by means of tin compounds $R_3SnOR'$ or $R_2SnO$ where R is lower alkyl resulting either directly in the desired anomeric compound or in a intermediate which is converted to the desired compound by silica or by acid hydrolysis.

15 Claims, No Drawings

ANOMERIC DEACETYLATION

BACKGROUND OF THE INVENTION

Sugars substituted at the anomeric position by a hydroxyl group (1—OH) are important intermediates in the synthesis of active pharmaceuticals. These include for example, intermediates useful in the synthesis of anticancer glycosides such as etopside and teniposide; anticancer aminoglycosides of the anthracycline family such as daunorubicin; and glucuronides possessing various biological activities, including treatment of malignant tumors (K. A. Watanabe, et al, J. Med. Chem., 24, 893 (1981); M. Kaneko et al., Chem. Pharm. Bull., 25, 2458 (1977): Europ. Pat. Appl. No. 82793). In addition compounds of Formula IV have been used in the preparation of glycosides and oligosaccharides, either as such, (N. Morishima, S. Koto, Chem. Lett., 1039 (1982)), or after being transformed into a more reactive moiety (R. R. Schmidt, M. Hoffman, Tetrahedron Lett., 23, 409 (1982)). The reported preparation of 1—OH sugars has involved heavy metal, primarily silver salt (silver oxide or silver carbonate) catalyzed solvolysis of 1-bromo sugars, (Org. Syn. Coll. Vol. 3, p 434; D. Keglevic, Adv. Carbohydr. Chem. Biochem., 36, 57 (1979)). This procedure, in addition of using expensive metal reagents, suffers also from the instability of the starting 1-halo derivatives which readily decompose even below room temperature.

Recently a procedure for the preparation of 1—OH and 1—OH-2-amino sugars derivatives was described, (Japanese Kokai: Tokkyo Koho J5 58, 144, 396), in which polyacetylated and 2-N-tosyl and 2-N-acetyl-polyacetylated sugars were treated with bis-tri-n-butyl-tin oxide in refluxing toluene for four hours to afford 65% of the corresponding 1—OH derivates. However, this process is cumbersome and inconvenient in its workup, since the side product of the reaction, which is tri-n-butyltin acetate, is difficult to remove from the reaction mixture and may contaminate the final product. Moreover this side product constitutes a waste of 50% of active tin reagent.

SUMMARY OF THE INVENTION

There is provided a process for the selective anomeric deacetylation of a wide variety of sugar derivatives. These may be substituted by various substituents, such as acetoxy, acyloxy, alkoxy, azido etc., to yield the desired product in high yields and in a high degree of purity. The anomeric deacetylation is carried out by reacting the starting material with a tin compound of the formula $R_3SnOR'$ where R and R' designate lower alkyl. The preferred tin compound is $(n\text{-butyl})_3SnOCH_3$. The reaction yields a compound which is substituted at the anomeric position by —O—Sn—$R_3$. The 1—O-tin derivative can be isolated as such or can be directly converted by hydrolysis to the corresponding 1—OH-sugar derivative. The reaction is set out in the enclosed reaction scheme where I designates the starting compound, with A designating the optionally substituted sugar moiety, and where I designates the tin compound used; III the 1—O-tin intermediate and IV the anomeric 1—OH-sugar, see reaction scheme. According to another embodiment of the invention, the starting compound I is reacted with a tin reagent of the formula II or V, i.e. $R_3SnOR'$ or $R_2SnO$, respectively where R and R' are as defined above, in an alcoholic solvent, preferably methanol, to give directly the desired product IV. The intermediate tin compounds III are novel compounds. Compounds of Formula III and IV are useful in the synthesis of various pharmaceutical products.

The reaction of the starting compound I with the tin compound $R_3SnOR'$ (II) is advantageously effected at a molar ratio from 1:1,5 to 1:1, preferably 1:1.1 in a volatile solvent, such as halogenated hydrocarbons, aromatic hydrocarbons and ethers. Preferred solvents are 1,2-dichloroethane, toluene and tetrahydrofuran (THF). The reaction time varies between ½ hour to 24 hours, preferably about 1 to 4 hours and the temperature of the reaction is about 20° to 100°, and preferably about 50° to 80°.

At the end of the reaction the solvent is removed and the residue of the formula III compound is crystallized from a suitable solvent, such as a hydrocarbon, preferably hexane. Compounds of formula III can be hydrolyzed and/or chromatographed to provide the formula IV products. The process of the invention is of a simple nature, it is inexpensive and has a high selectivity in providing products having the desired substitution at the anomeric position with a high yield and purity. According to another embodiment of the invention the starting material I is reacted with a tin reagent of the formula $R_3SnOR'$, II, wherein R and R' are lower alkyl, or with a tin compound of formula V, $R_2SnO$, where R is as above, in a suitable lower alkanol, such as methanol, ethanol, isopropanol, preferably methanol. The quantity of compound II or V used, ranges from catalytic to molar quantity per mole of compound I, preferably 0.3–0.5 mole per mole of I. Reaction times vary between half an hour to about 7 hours at a reaction temperature between 20° and 100°, preferably 25° to 65° C. At the end of the reaction the solvent is removed, resulting directly in the desired 1-hyroxy-sugar of Formula IV, which may be purified by crystallization from alkanols, preferably from ethanol, or by chromatography.

The removal of the acetyl group at the anomeric position is a highly selective one when the reaction is effected in alkanols. It is important not to exceed the required reaction period, of say 1 to 3 hours, as otherwise other acyloxy groups may also be removed. When carried out in a proper manner, a yield of about 80% of the desired product can be obtained.

The embodiment of the invention according to which the reaction is carried out in an alkanol such as methanol, ethanol, isopropanol, preferably methanol has the advantage of the use of a low boiling solvent and it requires only a small quantity of the tin compound. In addition tin compound V is a solid which is easily handled and it affords a high yield of the 1—OH-derivative.

According to the embodiments of the process of the invention the requirement for unstable 1-halo-sugar derivatives is obviated; there is no need to use expensive heavy-metal catalysts: the side products are easily removeable alkyl acetates and the process has a high selectivity for the anomeric position despite the lack of the anchimerically catalyzing neighboring 2-amino group or of derivatives thereof.

The invention is illustrated by the following examples, which are to be construed in a non-limitative manner.

GENERAL PROCEDURES FOR THE PREPARATION OF 1—OH SUGAR DERIVATIVES FROM THE CORRESPONDING 1—O-ACETYL SUGARS

Procedure (A) Tri-n-butyltin methoxide in an inert solvent

To a stirred solution of starting sugar (1 mmol), in a suitable solvent (10–20 ml) is added Bu$_3$Sn-OMe (1 mmol). The reaction mixture is stirred and refluxed under a nitrogen atmosphere for 1–3 hours. Two alternative work-up methods are used: (1) The solvent is removed under reduced pressure and the residue is subjected to flash chromatography (silica, eluent ethyl acetate-hexane 1:1); (2) The solution is extracted with dilute aqueous HCl, dried, evaporated to dryness and the residue triturated with hexane.

Procedure (B) Tri-n-butyltin methoxide in methanol

To a stirred mixture of starting sugar (1 mmol) in methanol (2–4 ml), is added Bu$_3$Sn-OMe (0.5 mmol). The mixture is heated to 50° C. until a clear, colorless solution is obtained and stirring is continued at this temperature for 2–4 hours. The solvent is removed under reduced pressure and the residue is purified by flash chromatography.

Procedure (C) Di-n-butyl tin oxide in methanol

To a stirred mixture of starting sugar (1 mmol) in methanol (6–10 ml), is added Bu$_2$SnO (0.7 mmol). The mixture is heated to 50° C. under stirring for 0.5–1.5 hours. The solvent is removed under reduced pressure and the residue is purified by chromatography.

EXAMPLE 1

2,3-Di-O-acetyl-4,6-O-ethylidene-D-glucopyranose is prepared in 77% yield from 1,2,3-tri-O-acetyl-4,6-O-ethylidene-β-D-glucopyranose according to Procedure A, by carrying out the reaction for 1 hour, in refluxing 1,2-dichloroethane.

EXAMPLE 2

2,3-Di-O-acetyl-4,6-O-ethylidene-D-glucopyranose is prepared in 75% yield from 1,2,3-tri-O-acetyl-4,6-O-ethylidene-β-D-glucopyranose according to Procedure A, by carrying out the reaction for 1.5 hours, in toluene at 95° C.

EXAMPLE 3

2,3-Di-O-acetyl-4,6-O-ethylidene-D-glucopyranose is prepared in 72% yield from 1,2,3-tri-O-acetyl-4,6-O-ethylidene-β-D-glucopyranose according to Procedure B, by carrying out the reaction for 3.5 hours, in methanol at 50° C.

EXAMPLE 4

2,3-Di-O-acetyl-4,6-O-ethylidene-D-glucopyranose is prepared in 65% yield from 1,2,3-tri-O-acetyl-4,6-O-ethylidene-β-D-glucopyranose according to Procedure C, by carrying out the reaction for 0.75 hours, in methanol at 50° C.

EXAMPLE 5

Methyl-2,3,4-tri-O-acetyl-D-glucopyranuronate is obtained in 78% yield from methyl-1,2,3,4-tetra-O-acetyl-β-D-glucopyranuronate according to Procedure A, by carrying out the reaction for 1.25 hours, in refluxing THF.

EXAMPLE 6

2,3,4,6-Tetra-O-acetyl-D-glucopyranose is obtained in 71% yield from 1,2,3,4,6-penta-O-acetyl-β-D-glucopyranose according to Procedure B, by carrying out the reaction for 3 hours, in methanol at 50° C.

EXAMPLE 7

2,3,4,6-Tetra-O-acetyl-D-glucopyranose is obtained in 60% yield from 1,2,3,4,6-penta-O-acetyl-β-D-glucopyranose according to Procedure C, by carrying out the reaction for 1.5 hours, in methanol at 50° C.

EXAMPLE 8

2,3,4,6-Tetra-O-acetyl-D-glucopyranose is obtained in 45% yield from 1,2,3,4,6-penta-O-acetyl-α-D-glucopyranose according to Procedure A, by carrying out the reaction for 1.5 hours, in refluxing toluene.

EXAMPLE 9

2,3,4,6-Tetra-O-acetyl-D-glucopyranose is obtained in 69% yield from 1,2,3,4,6-penta-O-acetyl-α-D-glucopyranose according to Procedure B, by carrying out the reaction for 3 hours, in methanol at 50° C.

EXAMPLE 10

2,3,4,6-Tetra-O-acetyl-D-galactopyranose is obtained in 80% yield from 1,2,3,4,6-penta-O-acetyl-β-D-galactopyranose according to Procedure A, by carrying out the reaction for 1.25 hours, in refluxing 1,2-dichloroethane.

EXAMPLE 11

2,3,4,6-Tetra-O-acetyl-D-galactopyranose is obtained in 26% yield from 1,2,3,4,6-penta-O-acetyl-α-D-galactopyranose according to Procedure A, by carrying out the reaction for 3 hours, in refluxing 1,2-dichloroethane.

EXAMPLE 12

2,3,4-Tri-O-acetyl-D-xylopyranose is obtained in 76% yield from 1,2,3,4-tetra-O-acetyl-β-D-xylopyranose according to Procedure A, by carrying out the reaction for 1.5 hours, in refluxing 1,2-dichloroethane.

EXAMPLE 13

2,3,4-Tri-O-acetyl-D-xylopyranose is obtained in 72% yield from 1,2,3,4-tetra-O-acetyl-β-D-xylopyranose according to Procedure B, by carrying out the reaction for 2 hours, in methanol at 50° C.

EXAMPLE 14

2,3,4-Tri-O-acetyl-D-xylopyranose is obtained in 58% yield from 1,2,3,4-tetra-O-acetyl-β-D-xylopyranose according to Procedure C, by carrying out the reaction for 0.75 hours, in methanol at 50° C.

EXAMPLE 15

2,3,5-Tri-O-acetyl-D-ribofuranose is obtained in 80% yield from 1,2,3,5-tetra-O-acetyl-β-D-ribofuranose according to Procedure A, by carrying out the reaction for 1 hour, in refluxing 1,2-dichloroethane.

EXAMPLE 16

2,3,5-Tri-O-benzoyl-D-ribofuranose is obtained in 75% yield from 1-O-acetyl-2,3,5-tri-O-benzoyl-β-D-ribofuranose according to Procedure A, by carrying out the reaction for 2.5 hours, in refluxing 1,2-dichloroethane.

NOTE: All the above described products are known compounds. The NMR spectra of the materials obtained as described above, conform to the expected structures.

separated, dried over $M_gSO_4$ and concentrated in vacuo. The residue was recrystallized from ether to give the title compound in 44% yield,

M.P.=115.120°.

Anal. Calcd for: $C_{14}H_{17}Cl_3O_8$; C, 38.58; H, 3.93; Cl, 24,44:

Found: C, 3850; H, 4.06; Cl, 24.23.

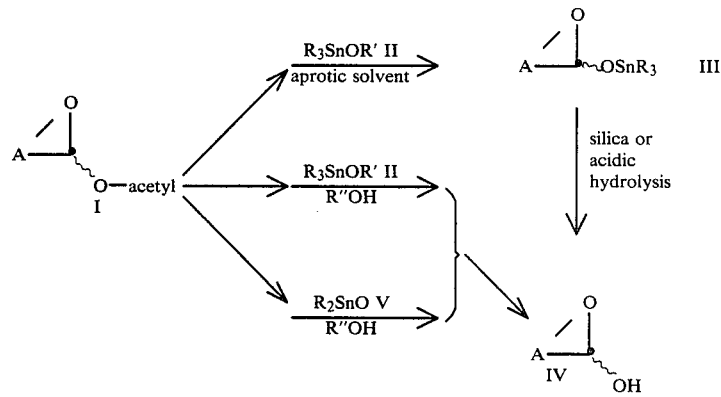

EXAMPLE 17

Tri-n-butyltin-(2,3-di-O-acetyl-4,6-O-ethylidene)-D-glucopyranoside.

To a stirred solution of 1,2,3-tri-O-acetyl-4,6-O-ethylidene-β-D-glucopyranose (133 g, 0.4 mole), in 1,2-dichloroethane (600 ml) is added $Bu_3$ Sn—OMe (128 g, 0.4 mole). The resulting solution is refluxed for 1 hour and the solvent is removed under reduced pressure, to afford the title compound in 100% yield, as a mixture of α and β anomers. Pure α-tri-n-butyltin-(2,3-di-O-acetyl-4,6-O-ethylidene)-D-glucopyranoside is crystallized from hexane, mp. 82°-85° C.

Anal. Calcd. for $C_{24}H_{44}O_8Sn$: C, 50.03; H, 7.17.

Found: C, 50.22; H, 7.47. NMR ($CDCl_3$) δ ppm: α-Anomer: 5.51 (t, 3-H), 5.31 (d, 1-H), 4.73 (dd, 2-H), 4.66 (q, Me-CH), 4.03 (dd, 6-H), 3.95 (ddd, 5-H), 3.5 (t, 6'-H), 3.35 (t 4-H), 2.05 (s, 3H, Ac), 2.025 (s, 3H, Ac), 1.58, 1.34, 1.14, 0.95 (m, 27H, n-Bu), 1.33 (d, Me-CH).

β-Anomer: 5.16 (dd, 3-H), 4.85 (d, 1-H), 4.71 (dd, 2-H) 4.66 (q, Me-CH), 4.12 (dd, 6-H); 3.52 (t, 6'-H), 3.42 (t, 4'-H), 2.045 (s, 3H, Ac), 2.03 (s, 3H, Ac), 1.58, 1.34, 1.14, 0.95 (m, 27H, n-Bu), 1.33 (d, Me-CH)

EXAMPLE 18

Tri-n-Butyltin-(2,3,4,6-tetra-O-acetyl)-D-Glucopyranoside

The title compound was obtained in direct analogy with the method of Example 17 except that 1,2,3,4,6-penta-O-acetyl-β-D-glucopyranose was used. High resolution mass spec fragment [M—$C_5H_9$] calcd for $C_{22}H_{37}O_{10}{}^{118}Sn$: 579.1402.

Found 579.1398 (100%).

Calcd. for $C_{22}H_{37}O_{10}{}^{120}Sn$: 581.1408.

Found 581.1377 (100%).

EXAMPLE 19

1,2,3-Tri-O-Chloroacetyl-4,6-O-Ethylidene-D-Glucopyranose

To a mixture of 31 g of chloroacetic anhydrine and 2.4 g of sodium acetate at 70° was added 5 g of 4,6-O-ethylidene glucose with stirring. After one hour at that temperature the reaction mixture was poured into ice, diluted with methylene chloride and ammonium hydroxide was added until basic. The organic phase was

We claim:

1. A process for the selective anomeric deacetylation of a sugar derivative, which comprises reacting such sugar derivatives of formula I:

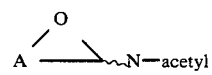

where

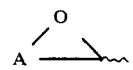

designates a ring structure selected from the group consisting of formulas (a)–(d) wherein the substituents R' are selected from the group consisting of acyl and alkoxy and wherein formulas (a)–(d) are as follows:

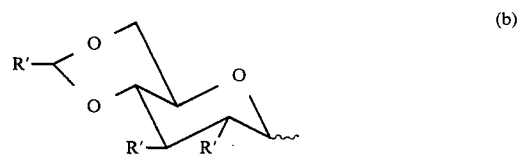

with a tin compound of the formula:

(R)₃SnOR' (II) or the formula (R)₂SnO, (V), wherein R and R' each designates lower alkyl, in an aprotic solvent to yield a 1–10 tin derivative of said ring structure where the anomeric carbon of said ring structure is substituted by the substituent —O—Sn—(R)₃, and hydrolyzing said 1-0 tin derivative to yield the corresponding desired deacetylated anomeric 1—OH-sugar; or reacting the starting substituted sugar derivative I in an alcoholic solvent with said tin compound (II) or (V) to yield the corresponding desired anomeric 1—OH-sugar.

2. A process according to claim 1, where the compound (II) is (n-butyl)₃Sn—O—CH₃.

3. A process according to claim 1, where the reaction of the Formula II tin compound is effected in an aprotic solvent at a molar ratio ranging from 1:1 to an excess of about 1.5 to 1 of the tin compound.

4. A process as claimed in claim 1, where the reaction temperature is from about 20° C. to about 100° C., to yield the 1-0 tin derivative where the anomeric position is —O—Sn(R)₃ substituted.

5. A process according to claim 4, wherein the hydrolysis is silica hydrolysis or an acid hydrolysis.

6. A process according to claim 3, wherein the tin compound is (n-butyl)₃Sn—O—CH₃ and the temperature of reaction is 50° C. to 80° C.

7. A process according to claim 1, where the reaction is effected in an alcoholic solvent, the tin compound being of the formula (R)₃SnOR' or (R)₂SnO, where R and R' each designates lower alkyl, the quantity of the tin compound being from a catalytic quantity and up to about a molar ratio of about 1 per mole of starting compound (I), to yield directly the anomeric 1—OH-sugar product.

8. A process according to claim 5, where the temperature of reaction is between 25° C. and 65° C.

9. A process according to claim 7, where the reaction is carried out for 0.5 to 4 hours, so as to remove essentially the 1-acetyl substituent only.

10. A process according to claim 7, where the reaction time is from 1 to 3 hours at a temperature of 65° C. or less.

11. A process according to claim 5, where the tin compound is (n-butyl)₃Sn—O—CH₃ or (n-butyl)₂SnO.

12. A sugar compound of the formula

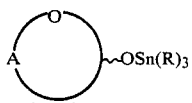

where the ring structure comprising A and O defines a sugar moiety, R is lower alkyl and —OSn(R)₃ is attached to the anomeric carbon of said sugar moiety and the ring structure designates a structure selected from the group consisting of formulas (a)-(d), wherein the substituents R' are selected from the group consisting of acyl and alkoxy and wherein formula (a)-(d) are as follows:

(a)

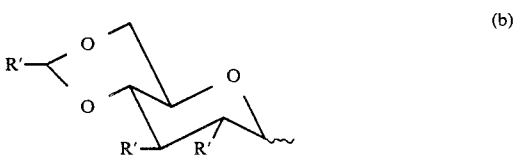

(b)

(c)

(d)

13. A compound according to claim 12, which is tri-n-butyltin-(2,3-di-O-acetyl-4,6-O-ethylidene)-O-glucopyranoside.

14. A compound according to claim 12 which is tri-n-butyltin-(2,3,4,6-tetra-O-acetyl)-O-glucopyranoside.

15. A compound according to claim 12, which is tri-n-butyltin-(2,3-di-O-chloroacetyl-4,6-O-ethylidene-O-glucopyranoside.

* * * * *

UNITED STATES PATENT AND TRADEMARK OFFICE
CERTIFICATE OF CORRECTION

PATENT NO. : 4,855,417

DATED : August 8, 1989

INVENTOR(S) : NUDELMAN et al.

It is certified that error appears in the above-identified patent and that said Letters Patent is hereby corrected as shown below:

In the Abstract: line 7, Delete "a", insert therefor -- an --

| | |
|---|---|
| Column 1, line 9 | Delete "etopside", insert therefor -- etoposide -- |
| Column 1, line 61 | Delete "I", insert therefor -- II -- |
| Column 5, line 54 | Delete "[M - $C_5H_9$]", insert therefor -- [M - $C_4H_9$] -- |
| Column 5, line 63 | Delete "anhydrine", insert therefor -- anhydride -- |
| Column 6, line 33 | Delete "N - acetyl", insert therefor -- O - acetyl -- |
| Column 7, line 4 | Delete "1-10 tin", insert therefor -- 1-O-tin -- |
| Column 7, line 10 | Delete "1-O tin", insert therefor -- 1-O-tin -- |

UNITED STATES PATENT AND TRADEMARK OFFICE
CERTIFICATE OF CORRECTION

PATENT NO. : 4,855,417

DATED : August 8, 1989

INVENTOR(S) : Nudelman, et al

It is certified that error appears in the above-identified patent and that said Letters Patent is hereby corrected as shown below:

Col. 7, line 25, Delete "1-0 tin", insert therefor --1-0-tin--

Signed and Sealed this

Third Day of December, 1991

*Attest:*

HARRY F. MANBECK, JR.

*Attesting Officer*  *Commissioner of Patents and Trademarks*